US006204258B1

(12) United States Patent
Smart et al.

(10) Patent No.: US 6,204,258 B1
(45) Date of Patent: *Mar. 20, 2001

(54) METHOD OF TREATING ALOPECIA

(75) Inventors: Robert C. Smart; Hye-Sun Oh, both of Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/257,396

(22) Filed: Feb. 25, 1999

Related U.S. Application Data

(63) Continuation of application No. 08/604,448, filed on Feb. 21, 1996, now Pat. No. 5,965,551.

(51) Int. Cl.$^7$ ................................................. A61K 31/56
(52) U.S. Cl. ........................ 514/178; 514/182; 514/880
(58) Field of Search ..................................... 514/178, 182, 514/324, 570, 651

(56) References Cited

U.S. PATENT DOCUMENTS

| | | | |
|---|---|---|---|
| 4,139,619 | 2/1979 | Chidsey, III | 424/45 |
| 4,596,812 | 6/1986 | Chidsey, III et al. | 514/256 |
| 4,828,837 | 5/1989 | Uster et al. | 424/450 |
| 5,026,691 | 6/1991 | Kligman | 514/171 |
| 5,068,315 | 11/1991 | Buultjens et al. | 530/324 |
| 5,177,061 | 1/1993 | Pickart | 514/18 |
| 5,183,814 * | 2/1993 | Dukes | 514/171 |
| 5,225,189 | 7/1993 | Pena | 424/70 |
| 5,348,729 * | 9/1994 | Sternberg et al. | 424/9 |
| 5,358,714 | 10/1994 | Green | 424/400 |
| 5,395,842 | 3/1995 | Labrie et al. | 514/320 |
| 5,407,944 | 4/1995 | Goldman | 514/310 |
| 5,574,048 | 11/1996 | Cullinan | 514/324 |
| 5,643,942 | 7/1997 | Hester, Jr. et al. | 514/456 |

FOREIGN PATENT DOCUMENTS

WO/96/01099   1/1996   (WO).

OTHER PUBLICATIONS

A.E. Wakeling et al.; A Potent Specific Pure Antiestrogen with Clinical Potential, *Cancer Res.* 51:3867–3873 (1991).

J. Bowler et al.; Novel Steroidal Pure Antiestrogens, *ICI Pharmaceuticals, Research Dept.* (1988).

H. Jiang et al.; Induction of Anagen in Telogen Mouse Skin by Topical Application of FK506, a Potent Immunosuppressant, *J. of Invest. Derm.* 104:523–525 (1995).

J.P. Jacobs et al.; Use of Topical Minoxidil Therapy for Androgentic Alopecia in Women, *Int'l J. of Derm.* 32:758–762 (1993).

D.H. Rushton; Management of Hair Loss in Women, *Derm. Therapy* 11 No. 1:47–53 (1993).

G. Bazzano et al.; Effect of Retinoids on Follicular Cells, *J. of Invest. Derm.*, 101 No. 1 (Supp):138S–142S (1993).

H. Uno et al.; Chemical Agents and Peptides Affect Hair Growth, *J. of Invest. Derm.* 101 No. 1, (Supp) 138S–142S (1993).

W.S. Branham et al.; ICI 182,780 Inhibits Endogenous Estrogen–Dependent Rat Uterine Growth and Tamoxifen––Induced Development Toxicity, *Bio of Reproduct* 54:160–167 (1996).

C. Levesque et al.; Synthesis and Biological Activity of New Halo–Steroidal Antiestrogens, *J. Med. Chem.* 34:1624–1630 (1991).

A. Claussner et al.; 11 β–Amidoalkyl Estradiols, A New Series of Pure Antiestrogens, *J. Steroid Biochem. Molec. Biol.* 41 No. 3–8:609–614 (1992).

D. Poirier et al; Synthesis and Antiestrogenic Activity of Diaryl Thioether Derivatives, *J. Med. Chem.* 37:1115–1125 (1994).

V.C. Jordan; Hydroxylated Antioestrogens: New Pharmacological Probes to Investigate Oestrogen and Antioestrogen Action, *Hormone Antagonists* 110–111 (1982).

J. Rosen et al.; Intracellular Receptors and signal Transducers and Activators of Transcription Superfamilies: Novel Targets for Small–Molecule Drug Discovery, *J. Med. Chem.* 38 No. 25:4855–4874 (1995).

* cited by examiner

*Primary Examiner*—Rebecca Cook
(74) *Attorney, Agent, or Firm*—Myers Bigel Sibley & Sajovec

(57) ABSTRACT

A method of enhancing hair growth or treating alopecia in a subject uses topically administered estrogen receptor antagonists. Pharmaceutical formulations comprising estrogen receptor antagonists are described.

8 Claims, 15 Drawing Sheets

METHOD OF TREATING ALOPECIA

This application is a continuation of Ser. No. 08/604,448, filed on Feb. 21, 1996, now U.S. Pat. No. 5,965,551.

This invention was made with Government support under grant CA46637 from the National Cancer Institute and grant ES07046 from the National Institute for Environmental Health Sciences. The Government has certain rights to this invention.

FIELD OF THE INVENTION

This invention relates to methods of treating hair loss and promoting hair growth, and more particularly to a method of using estrogen receptor antagonists to promote hair growth in a subject in need of such treatment.

BACKGROUND OF THE INVENTION

Alopecia (baldness) is a deficiency of hair, either normal or abnormal, and is primarily a cosmetic problem in humans, although the negative psychological impact of hair loss is well known. See C. H. Mortimer et al., *Clin. Exp. Dermatol.* 9, 342–350 (1984). Dermatologists recognize many different types of alopecia, with androgenic alopecia being the most common cause of hair loss in both men and women. As this type of hair loss is more common and more severe in males, it is typically referred to as "male pattern baldness." However, it is thought that androgenic alopecia affects more that one third of individuals of either sex who have a strong family history of hair loss. See W. F. Bergfield, *Clin. Dermatol.* 6, 102–107 (1988).

One traditional treatment for alopecia is the method of hair transplantation. Typically, this method involves transplanting plugs of natural hair from areas of the scalp where hair is growing to bald areas. This procedure is costly, time-consuming, painful, and meets with only limited success.

Another common treatment for hair loss is the application of a chemical or drug for the purpose of stimulating hair growth. For example, U.S. Pat. No. 5,177,061 to Pickart proposes the topical application of glycyl-L-histidyl-L-lycine:copper(II) (GHL-Cu) and its derivatives to promote hair growth in warm-blooded animals (applicant specifically intends the disclosure of this and all other patent references cited herein to be incorporated herein by reference in their entirety). U.S. Pat. No. 4,832,946 to Green proposes a composition for topical application to mammalian hair or skin, comprising an amount of the cell-free supernatant from a culture of dermal papilla fibroblasts, which is said to increase hair growth in the rat. U.S. Pat. No. 5,358,714 to Green proposes the use of diacylglycerol activators of protein kinase C in order to increase or maintain hair growth in mammals, while U.S. Pat. No. 5,068,315 to Buultjens et al. proposes the application of purified hair growth regulating peptides (HGRP) to stimulate hair growth. It has also been suggested that retinoids, substituted pyrimidines, and immunosuppressants be used as possible treatments for hair loss, although methods utilizing these compounds have not been entirely successful in producing a reliable and safe method of inducing hair growth. See G. Bazzano et al., *J. Invest. Dermatol.* 101 (1 Supplement), 138S–142S (1993); H. Jiang et al., *J. Invest. Dermatol.* 104(4), 523–525 (1995).

In recent years, the topical application of minoxidil has been a widely-used method for treating androgenic alopecia. See A. R. Zapacosta, *N. Eng. J. Med.* 303, 1480–81 (1980). U.S. Pat. No. 4,139,619 to Chidsey, proposes a topical composition of minoxidil and related iminopyrimidines to stimulate the conversion of vellus hair to terminal hair and increase the rate of growth of terminal hair. However, despite its popularity, minoxidil has not performed in a completely satisfactory fashion in promoting hair growth in all target populations.

SUMMARY OF THE INVENTION

A first aspect of the present invention is a method of treating alopecia in a subject in need thereof. The method comprises topically applying to the skin of the subject an estrogen receptor antagonist or a pharmaceutically acceptable salt thereof (an "active compound") in an amount sufficient to treat alopecia.

A more general aspect of the present invention is a method of promoting hair growth in a subject in need thereof. The method comprises topically applying to the skin of the subject an active compound as given above in an amount sufficient to promote hair growth.

A second aspect of the present invention is a topical pharmaceutical formulation comprising an active compound as given above in an amount effective to treat alopecia or promote hair growth, in a pharmaceutically acceptable topical carrier.

A third aspect of the present invention is the use of an active compound as given above for the preparation of a medicament useful for carrying out a method as given above.

DETAILED DESCRIPTION OF THE INVENTION

Figure 1A:
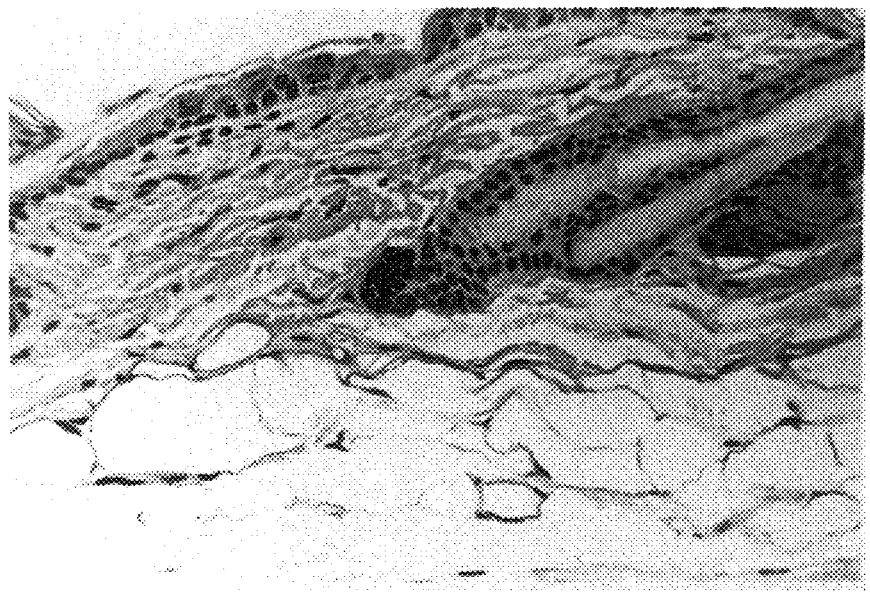
FIG. 1A is a photomicrograph showing the immunohistochemical localization of estrogen receptors in telogen hair follicle tissue from mouse skin, where immunohistochemical staining was conducted with hematoxylin counterstaining.

The method of the present invention is useful in the treatment of alopecia in mammals, and as such may be used to promote, increase, or assist in the growth of hair. Subjects may be male or female. As used herein, the term alopecia refers to the complete absence of hair in skin which typically exhibits hair growth, as well as a loss or diminution in the amount of hair. Multiple types and causes of alopecia are recognized in humans, including male pattern baldness, chemotherapy induced hair loss, congenital alopecia, and alopecia areata. As used herein, the term 'treating alopecia' refers to both the treatment of skin with a total absence of hair growth as well as treatment of skin having reduced or patchy hair growth.

The present invention is concerned primarily with the treatment of human subjects but may also be employed for the treatment of other mammalian subjects, such as dogs, cats, and sheep, for veterinary purposes (e.g., in the treatment of hair loss due to mange or other causes, or for enhancing wool or pelt production).

Hair, or pili, are fine threadlike appendages of the skin which normally cover the entire body (with the exception of the palms of the hands and soles of the feet, and the flexor surfaces of joints). A hair comprises a root embedded in the hair follicle and a free portion (the stem or shaft). As used herein, hair refers to mature hair as well as the soft, downy hair known as vellus hair.

The hair bulb, or follicle, is a compact structure located in the dermis layer of the skin and is composed of three main cellular groups. The first comprises a compact group of fibroblasts known as the dermal papilla which includes a capillary system. The second group comprises germinative epithelial cells of the hair bulb which proliferate and differentiate to give rise to the mature hair shaft. The third group of fibroblasts exists around the outside of the bulb in the connective tissue sheath.

The present invention is, in general, carried out with estrogen receptor antagonists. The term "antagonist," as used herein, refers to compounds that act as complete or partial inhibitors of the activity of a biological substance by specifically binding to the receptor thereof. Numerous estrogen receptor antagonists are known in the art. It is specifically intended that both full and partial estrogen receptor antagonists are embraced by the scope of the invention, although full estrogen receptor antagonists are preferred.

Estrogen receptor antagonists may be steroids or non-steroid compounds. In one preferred embodiment of the invention, the estrogen receptor antagonist is a steroid. Particularly preferred are 7α-alkylamide analogs of estradiol, 11β-alkylamide analogs of estradiol and 16α-halo-17β-estradiols that have pure antiestrogenic activity.

In a preferred embodiment of the invention, the estrogen receptor antagonist is a compound of Formula I:

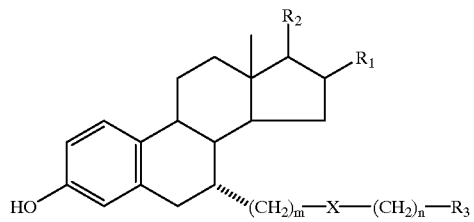

wherein m is from 1 to 15;
n is from 1 to 5;
$R_1$ is hydrogen, lower alkyl, or halogen;
$R_2$ is oxygen or hydroxyl;
$R_3$ is lower alkyl or haloalkyl; and
X is

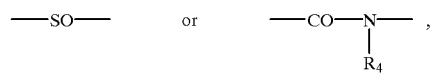

wherein $R_4$ is loweralkyl.

Estrogen receptor antagonists suitable for use in the present invention include, but are not limited to, 7α-[9-(4,4,5,5,5,-pentafluoropentylsulfinyl)nonyl]estra-1,3,5(10)-triene-3,17β-diol (also known as ICI 182,780), N-n-butyl-N-methyl-11-(3,17β-dihydroxyestra-1,3,5(10)-triene-7α-yl) undecanamide (also known as ICI 164,384), 11β-[4-[2-(dimethylaminoethoxy]phenyl]-estradiol (also known as RU 39411), N-methyl-N-isopropyl-(3,17β-dihydroxy-estra-1,2,5(10)-trien-11-β-yl)-undecamide (RU 51625), its 17α-ethynyl derivative (RU 53637), [6-hydroxy-2(4-hydroxyphenyl)benzo[b]thien-3-yl] [4-[3-(1-pyrrolidin-yl)ethoxy]phenyl]methanone (LY117018), tamoxifen, clomiphene, keoxifene, 3-[4-(1,2-Diphenylbut-1-enyl)phenyl]acrylic acid, and the like, including the active metabolites of these compounds. These compounds may be made in accordance with known procedures which will be apparent to those skilled in the art. See, e.g., A. E. Wakeling et al., *Canc. Res*, 51, 3867–3873 (1991); D. Poirier et al., *J. Med. Chem*, 37, 1115–1125 (1994); J. Bowler et al. *Steroids* 54, 71–79 (1989); C. Levesque et al., *J. Med. Chem*, 34, 1624–1630 (1991); A. Claussner et al., *J. Steroid. Biochem. Mol. Biol*, 41, 609–614 (1992).

The active compounds described herein can, as noted above, be prepared in the form of their pharmaceutically acceptable salts. Pharmaceutically acceptable salts are salts that retain the desired biological activity of the parent compound and do not impart undesired toxicological effects. Examples of such salts include (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine; and (c) salts derived from bases, such as ammonium salts; alkali metal salts such as those of sodium and potassium; alkaline earth metal salts such as those of calcium and magnesium; and salts with organic bases such as dicyclohexylamine and N-methyl-D-glucamine.

The dosage of the active compound is not particularly critical so long as it achieves the desired effect. Actual dosage will depend on factors such as the particular pharmaceutical carrier, the particular skin region and condition being treated, and the general health and condition of the subject. In one embodiment of the invention, the active compound is topically administered to the affected skin of a subject in an amount sufficient to achieve a dose of at least 0.01 nanomoles (nmol), 0.1 nmol, or 1 nmol per 2 cm by 4.5 cm skin surface area, up to a dose of 100 nmol, 1,000 nmol, or 10,000 nmol or more per 2 cm by 4.5 cm skin surface area.

Depending on the solubility of the particular formulation of active compound administered, the daily dose may be divided among one or several unit dose administrations. The dose may be a single unit dose, which may, for example, be administered several times a week or from 1 to 3 times a day. Treatments may continue week to week on a chronic basis as necessary (i.e., the active agent can be administered chronically). Administration of the active compounds may be carried out therapeutically or prophylactically, but preferably the compounds are administered therapeutically, either before substantial hair loss has occurred, or at a time when such hair loss has just begun.

Pharmaceutical compositions for use in the present method include those suitable for topical administration. The compositions may conveniently be presented in unit dosage form and may be prepared by any of the methods well known in the art. The most suitable route of administration in any given case may depend upon the anatomic location of the alopecia in the subject, the nature and severity of the condition being treated, and the particular active compound which is being used.

Pharmaceutical compositions useful in the present methods are preferably applied topically at the site of the affected skin. In alternative embodiments of the invention, pharmaceutical compositions useful in the present invention may be administered to a subject orally, parenterally (e.g., subcutaneously, intravenously, or intramuscularly), or transdermally (e.g., at a site other than the affected area to achieve systemic administration).

In a further aspect of the present invention, estrogen receptor antagonists may be used alone or in combination with one or more anti-alopecics for the prophylaxis or treatment of alopecia.

In the manufacture of a medicament according to the invention (a "formulation"), active agents or the physiologically acceptable salts thereof (the "active compound") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, an aliquot of ointment which may contain from 0.001% to 99% by weight of the active compound. One or more active compounds may be incorporated in the formulations of the invention (e.g., the formulation may contain one or more additional anti-alopecia agents as noted above), which formulations may be prepared by any of the well known techniques of pharmacy consisting essentially of admixing the components, optionally including one or more accessory therapeutic ingredients.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Additionally, the compounds of the present invention may be administered by a liposome delivery system, as detailed in U.S. Pat. No. 4,828,837 to Uster et al.

The compounds useful in the method of the present invention may be applied the surface of the skin at any anatomical location in need of treatment on the subject, including the scalp, pubis, face, chest, and legs. Administration of the compounds of the present invention onto the scalp of the subject is a preferred embodiment of the invention.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder. Formulations for oral administration may optionally include enteric coatings known in the art to prevent degradation of the formulation in the stomach and provide release of the drug in the small intestine.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

Formulations suitable for transdermal administration (either at the site in need of treatment or at another site to achieve systemic administration) may be presented as discrete patches adapted to remain in intimate contact with the epidermis of the recipient for a prolonged period of time. Formulations suitable for transdermal administration may also be delivered by electrophoresis or iontophoresis (see, e.g., *Pharmaceutical Research* 3, 318 (1986)) and typically take the form of an optionally buffered aqueous solution of the active compound.

Although applicants do not wish to be bound to any particular theory of the instant invention, it appears that estrogen receptor antagonists cause telogen-phase hair follicles (resting follicles) to enter the anagen phase (active follicle) cycle, which results in the production of hair fiber and hair growth. Normally, approximately 90% of scalp hairs are in the anagen phase, with less than 1% in an intermediate catogen phase and the rest in telogen. With the onset of patterned baldness, however, a successively greater proportion of hairs are in telogen, while correspondingly fewer are found in the anagen phase.

The following examples are provided to more fully illustrate the present invention and should not be construed as limiting thereof. As used in the following examples, 17-β Estradiol was purchased from Sigma Chemical Company (St. Louis, Mo., USA); ICI 182,780 was a gift from Zeneca Pharmaceuticals (Cheshire, England); link antibody, labal antibody and 3,3'-diaminobenzidine tetrahydrochloride/ Super Sensitive Multi-link Immunostaining Kit were purchased from Biogenex Laboratorie (San Ramon, Calif., USA); 10× Automation Buffer was purchased from Biomeda Corporation, (Foster City, Calif., USA).

EXAMPLE 1

Animals and Estrogen or Estrogen Receptor Antagonist Treatment

Female CD-1 mice, 4, 5, or 9 weeks of age, were purchased from Charles River Laboratories, Raleigh, N.C. Mice were kept in an animal facility at least 1 week prior to use and were fed rodent chow (Agway Food, Granville Milling and Co., Creedmoor, N.C.) and water ad libitum. The mice were kept on corn cob bedding and placed on a 12 hour light/dark cycle. Female CD-1 mice were clipped on the dorsal region (approximately 4–2.5 cm area) with electric clippers. The mice were then treated twice weekly on the clipped dorsal surface with either (a) 10 nmol 17-β-estradiol in 200 µl acetone or (b) acetone alone. For the studies with the estrogen receptor antagonist, ICI 182,780 was dissolved in acetone and 200 µl was topically applied twice weekly.

EXAMPLE 2

Localization of Estrogen Receptor in Mouse Skin

Seven-week-old female CD-1 mice were killed by cervical dislocation and the dorsal skin area was excised. The skins were fixed for 24 hours in a cold 10% neutral buffered formalin, then changed to cold 70% ethanol and processed and embedded in paraffin. Tissue sections were cut at 5 µm and placed on SuperFrost Plus slides for immunohistochemistry. In order to localize the estrogen reception in skin, the paraffin sections were deparaffinized by two changes of xylene and rehydrated in a graded series of ethanol (100, 95 and 70%) followed by 1× automation buffer. The skin sections were placed in 3% $H_2O_2$ for 10 min to quench the endogenous peroxidase activity and then washed with 1× automation buffer. The sections were treated with fresh trypsin of 0.15 mg/ml in 1× automation buffer for 4 min at room temperature followed by 1× automation buffer twice and incubated with fresh DNAase of 0.25 mg/ml in 1× automation buffer for 3 min at room temperature followed by 1× automation buffer twice. The sections were blocked with 10% normal goat serum in 1× automation buffer for 15 min at room temperature. After blocking, the excessive solution was drained, and a prediluted primary antibody (Abbott ER-ICA monoclonal antibody, Abbott Laboratories, North Chicago, Ill.) was applied and incubated overnight at 4° C. Slides were washed in 1× automation buffer for 5 min twice and a secondary antibody (biotinylated goat anti-rat IgG, Boehringer Mannheim Corporation, Indianapolis, Ind.) at a dilution of 1:50 in 1× automation buffer was applied for 60 min at room temperature. After washing with 1× automation buffer for 5 min twice, the sections were incubated with peroxidase (HRP)-conjugated streptavidin (1:20 dilution, BioGenex, San Ramon, Fla.) for 30 min at room temperature and washed with 1× automation buffer for 5 min and 0.05M Tris-HCl (pH 7.5) for 5 min. The sections were then incubated with DAB (prepared according to the manufacturer's instruction) for 10 min in a dark box. Slides were rinsed with 0.05M Tris-HCl buffer twice and counterstained in hematoxylin for 5 seconds followed by rinsing in distilled water five times. Finally, the sections were dehydrated in a graded series of ethanol and xylene, and then slides were permanently mounted with Permount.

Figure 1B:
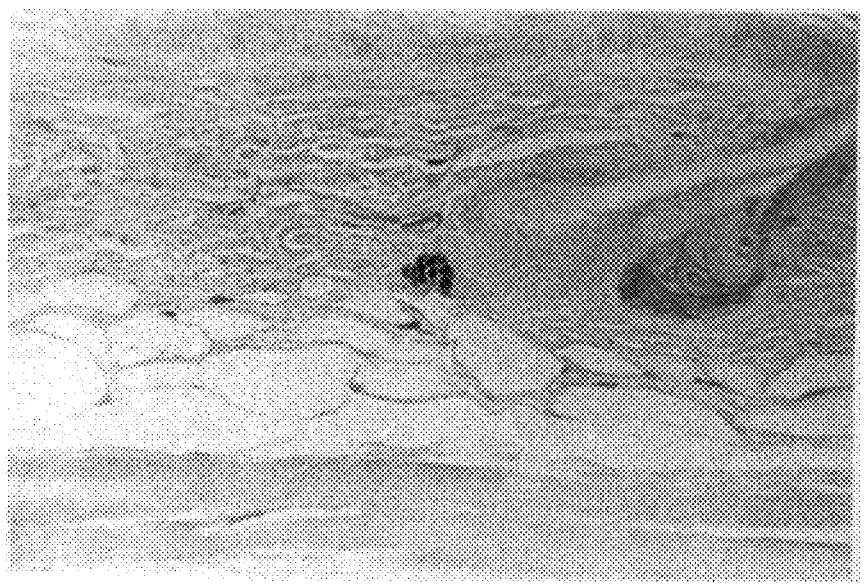
FIG. 1B is photomicrograph showing the immunohistochemical localization of estrogen receptors in telogen hair follicle tissue from mouse skin, where immunohistochemical staining was conducted without hematoxylin counterstaining.
Figure 1C:
FIG. 1C is photomicrograph showing the immunohistochemical localization of estrogen receptors in early-anagen hair follicle tissue from mouse skin, where immunohistochemical staining was conducted with hematoxylin counterstaining.
Figure 1D:
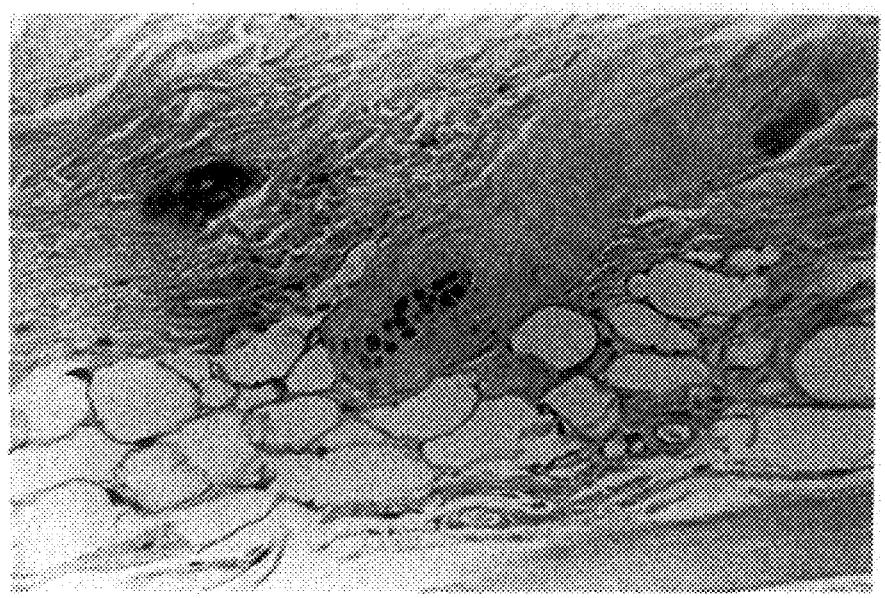
FIG. 1D is photomicrograph showing the immunohistochemical localization of estrogen receptors in early-anagen hair follicle tissue from mouse skin, where immunohistochemical staining was conducted without counterstaining.

Immunohistochemical staining for the estrogen receptor in mouse skin revealed intense and specific staining of the nuclei of cells with the dermal papilla of a telogen follicle, as shown in the counterstained sample FIG. 1A. Non-counterstained samples (FIG. 1B) are provided to better demonstrate the areas and levels of estrogen receptor expression. Estrogen receptor expression within most telogen dermal papilla demonstrated a polarity, as nuclei of cells within the lower half of the dermal papilli stained intensely, while very little staining was observed in the upper half of dermal papilla. In addition, the expression of the estrogen receptor was hair cycle dependent as there was a weaker staining of the dermal papilla of mid to late catagen or anagen follicles (FIGS. 1C and 1D), and no detectable staining in dermal papilla of mid to late anagen follicles (data not shown). Very light estrogen receptor staining was observed in cells of the outer root sheath in the isthmus of the telogen follicle as well as in some nuclei of dermal fibroblasts.

EXAMPLE 3

Estrogen Receptor Antagonist ICI 182,780 Induces Hair Growth

Figure 2:
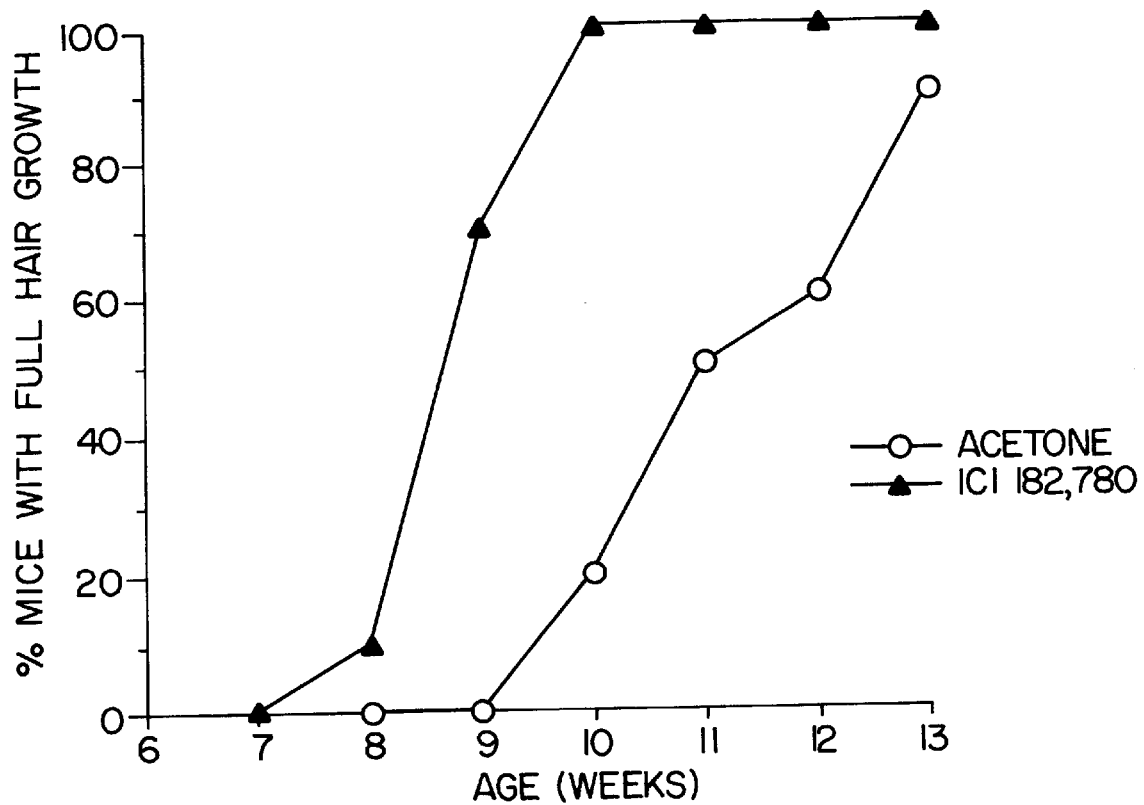
FIG. 2 is a graph illustrating that the estrogen receptor antagonist ICI 182,780 causes hair growth during the second telogen phase in mice. Closed triangles represent mice treated with 10 nmol ICI 182,780 in 200 $\mu$L acetone applied topically to an area of clipped hair. Open circles represent control mice treated with 200 $\mu$L acetone alone.
Figure 3A:
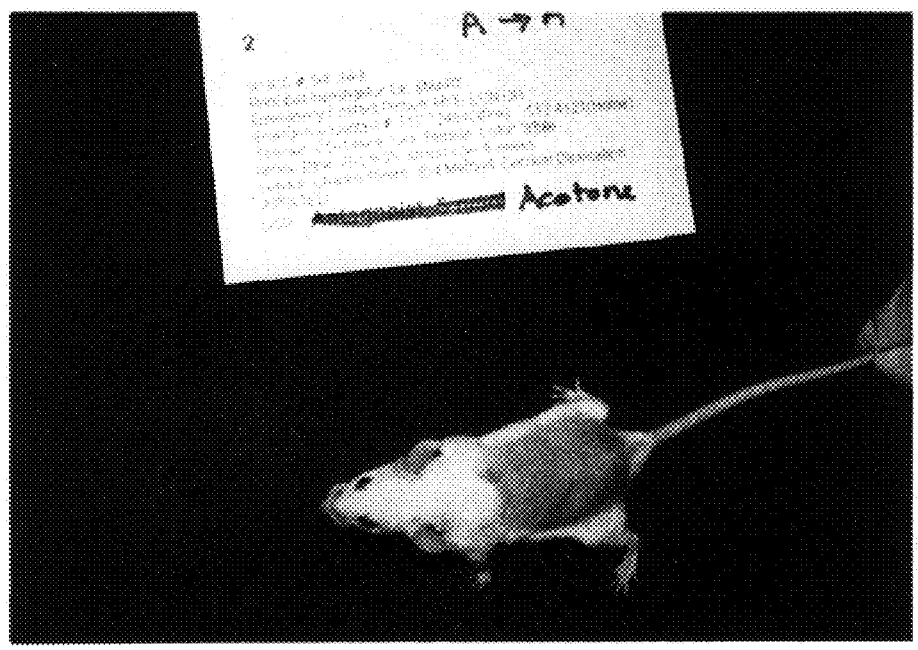
FIG. 3A is a photograph of a mouse treated with 200 $\mu$L of acetone applied topically to an area of clipped hair twice a week.
Figure 3B:
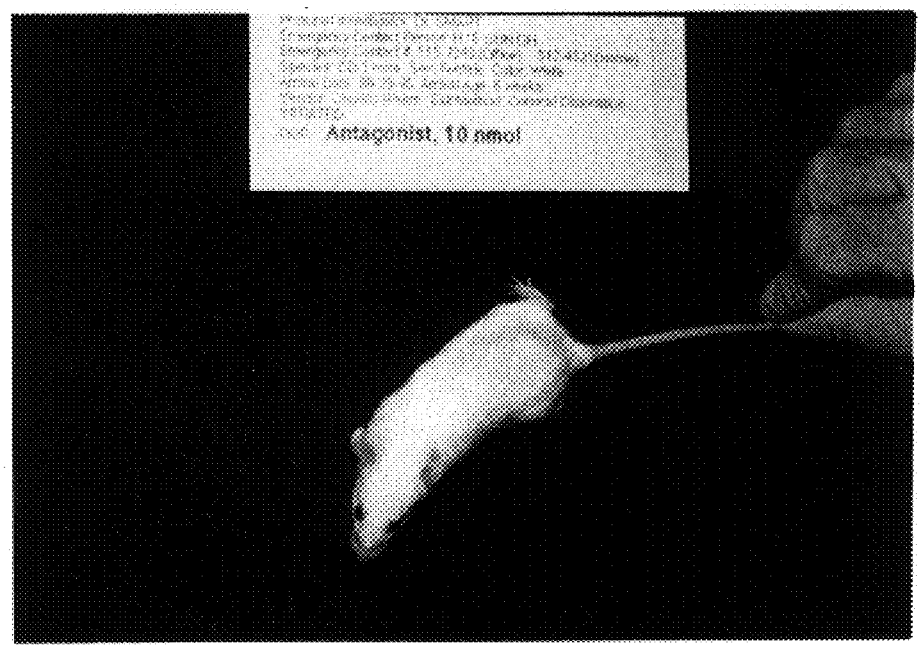
FIG. 3B is a photograph of a mouse treated with 10 nmol ICI 182,780 in 200 $\mu$L acetone applied topically to an area of clipped hair twice a week.

Mice were treated with the estrogen receptor antagonist ICI 182,780 as provided in Example 1. Twice-weekly treatment of clipped dorsal skin was begun when the mice were 6 weeks of age, with either (a) 10 nmol ICI 182,780 in acetone or (b) acetone alone. As shown in FIG. 2 and FIG. 3, by 9 weeks of age, 60% of the ICI 182,780 treated mice demonstrated full hair regrowth while no hair growth was observed in the acetone treated mice. By 10 weeks of age all of the ICI 182,780 treated mice developed a full coat of hair while only 40% of the acetone-treated mice demonstrated full hair regrowth.

Figure 4A:
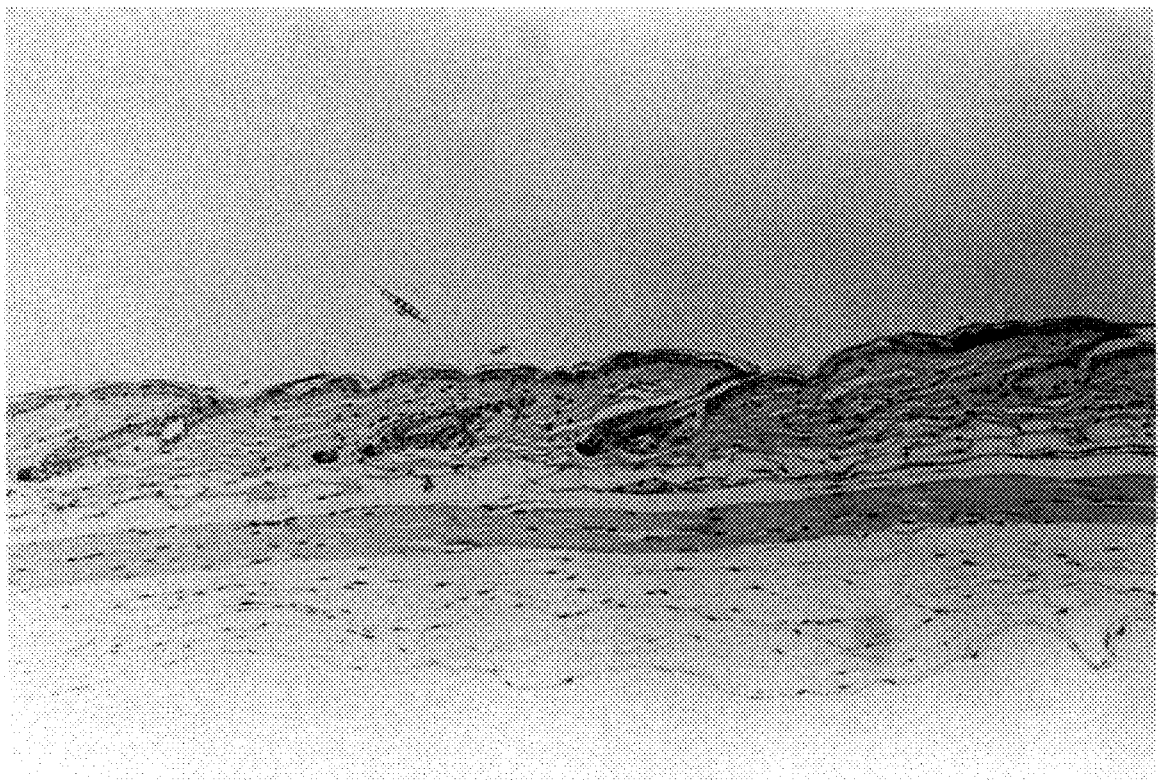
FIG. 4A is a photomicrograph of skin tissue from a six-week-old mouse treated with 200 $\mu$L of acetone applied topically to an area of clipped hair twice a week until seven weeks of age. The tissue was stained with hematoxylin/eosin.
Figure 4B:
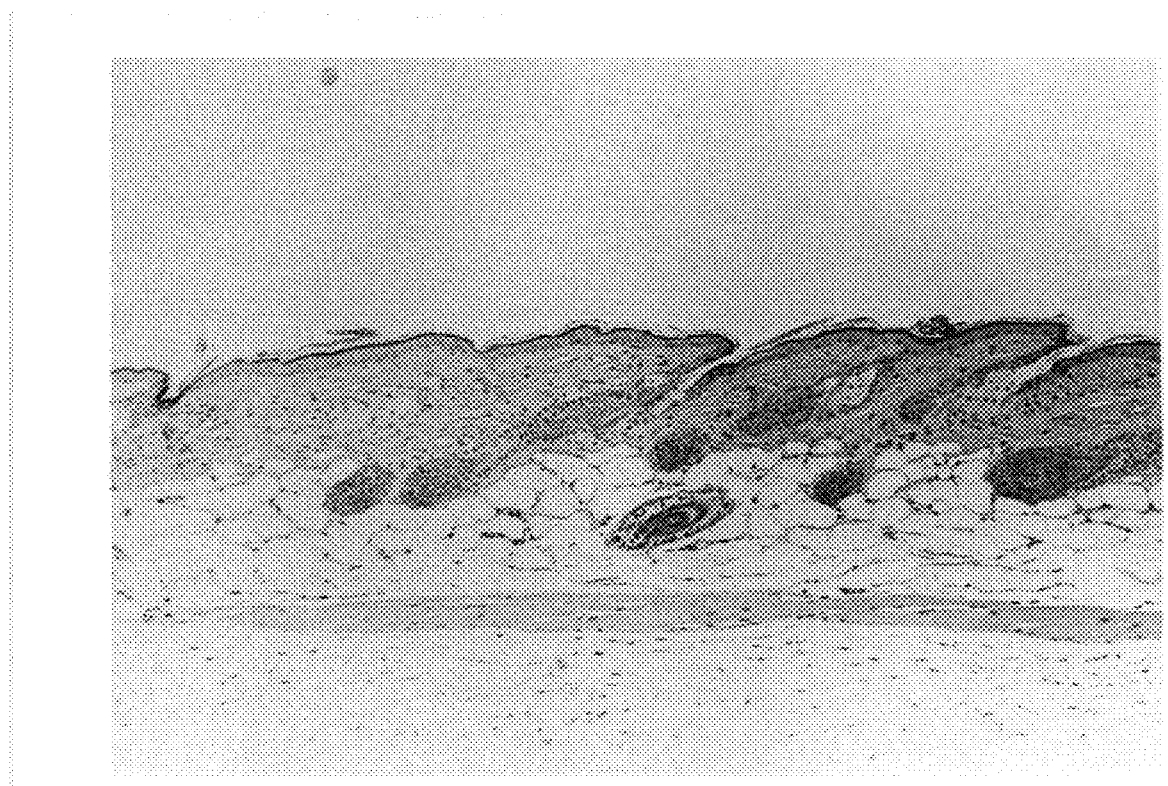
FIG. 4B is a photomicrograph of skin tissue from a six-week-old mouse treated with 10 nmol ICI 182,780 in 200 μL acetone applied topically to an area of clipped hair twice a week until seven weeks of age. The tissue was stained with hematoxylin/eosin.
Figure 4C:
FIG. 4C is a photomicrograph of skin tissue from a six-week-old mouse treated with 200 μL of acetone applied topically to an area of clipped hair twice a week until eight weeks of age. The tissue was stained with hematoxylin/eosin.
Figure 4D:
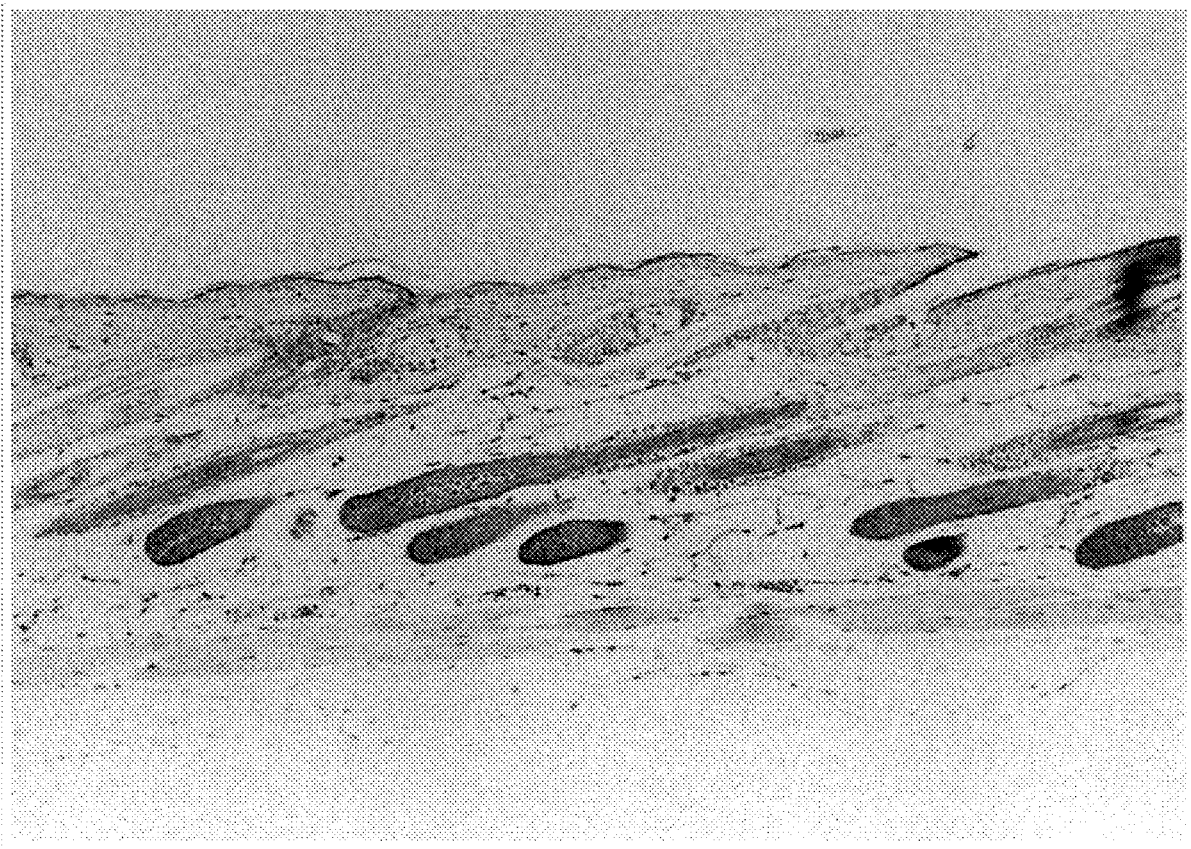
FIG. 4D is a photomicrograph of skin tissue from a six-week-old mouse treated with 10 nmol ICI 182,780 in 200 μL acetone applied topically to an area of clipped hair until eight weeks of age. The tissue was stained with hematoxylin/eosin.

These data indicate that ICI 182,780 caused the telogen follicle to enter anagen during what should have been the second synchronized telogen phase. The confirm this result, skin was collected and prepared for histological analysis at 7, 8, 9, 10 and 11 weeks. At 7 weeks of age the ICI 182,780 treated mice demonstrated follicles that were already in early to mid anagen, while the follicles of the acetone-treated mice were synchronized in second telogen (FIGS. 4A and 4B). By eight weeks of age the follicles of the ICI 182,780 treated mice demonstrated follicles that were in mid to late anagen while the hair follicles in acetone-treated mice were in telogen (FIGS. 4C and 4D). These results indicate that the estrogen receptor antagonist ICI 182,780 initiates the transition of a telogen follicle into anagen. At eleven weeks of age, the follicles of mice treated with ICI 182,780 entered telogen, while control mice were in mid to late anagen (data not shown), indicating that ICI 182,780 does not prolong anagen.

EXAMPLE 4

17-β Estradiol Inhibits Hair Growth

Figure 5:
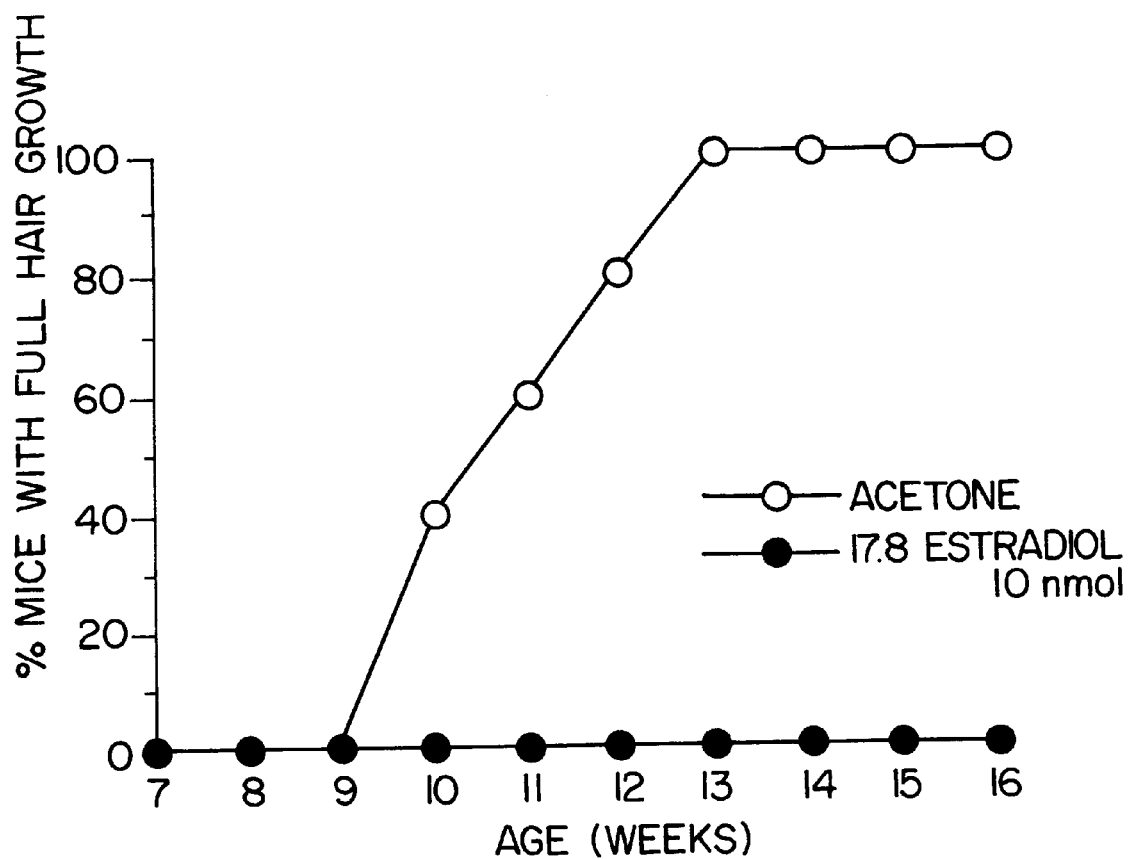
FIG. 5 is a graph illustrating that topical 17β-estradiol blocks hair regrowth in mice. Six week old mice (5 mice per group) were clipped and treated with topical applications of either 10 nmol 17β-estradiol in 200 μL acetone (closed circles) or acetone alone (open circles), twice a week, up to sixteen weeks of age.
Figure 6A:
FIG. 6A is a photomicrograph of skin tissue from a mouse, where 200 μL of acetone was applied topically to shaved skin twice a week for three weeks. Tissue is stained with hematoxylin/eosin.
Figure 6B:
FIG. 6B is a photomicrograph of skin tissue from a mouse, where 10 nmol 17β-estradiol in 200 μL acetone was applied topically to shaved skin twice a week for three weeks. Tissue is stained with hematoxylin/eosin.
Figure 6C:
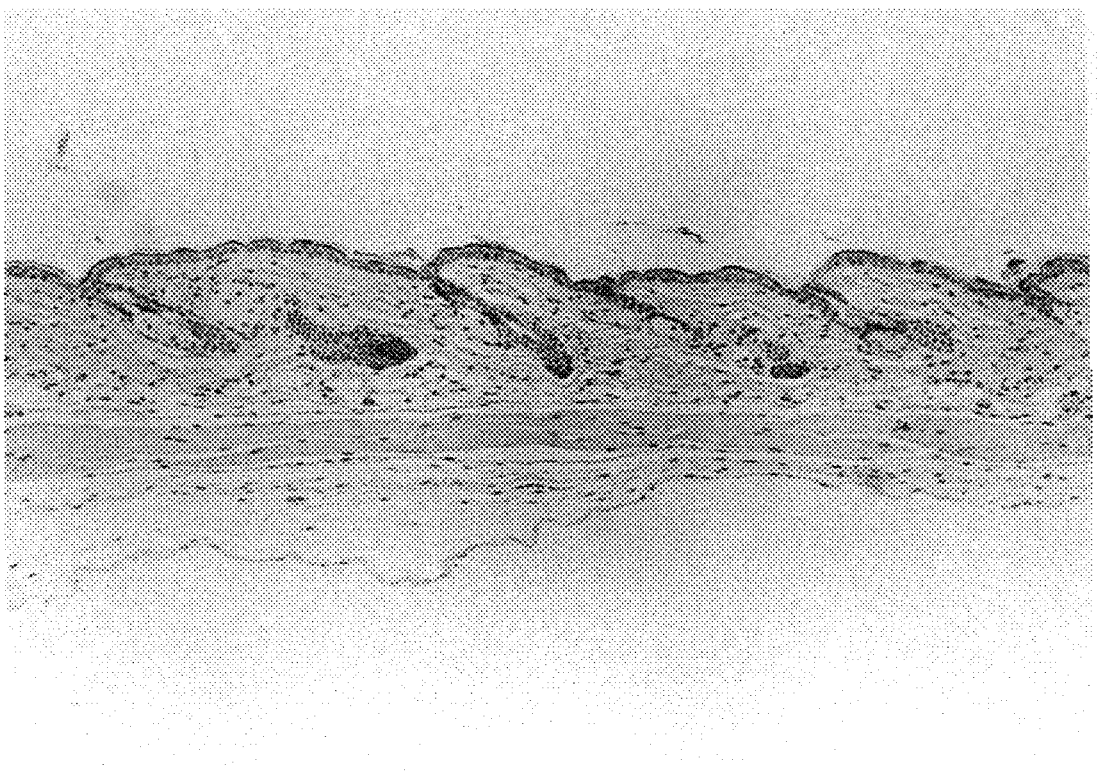
FIG. 6C is a photomicrograph of skin tissue from a mouse, where 200 μL of acetone was applied topically to shaved skin twice a week for five weeks. Tissue is stained with hematoxylin/eosin.
Figure 6D:
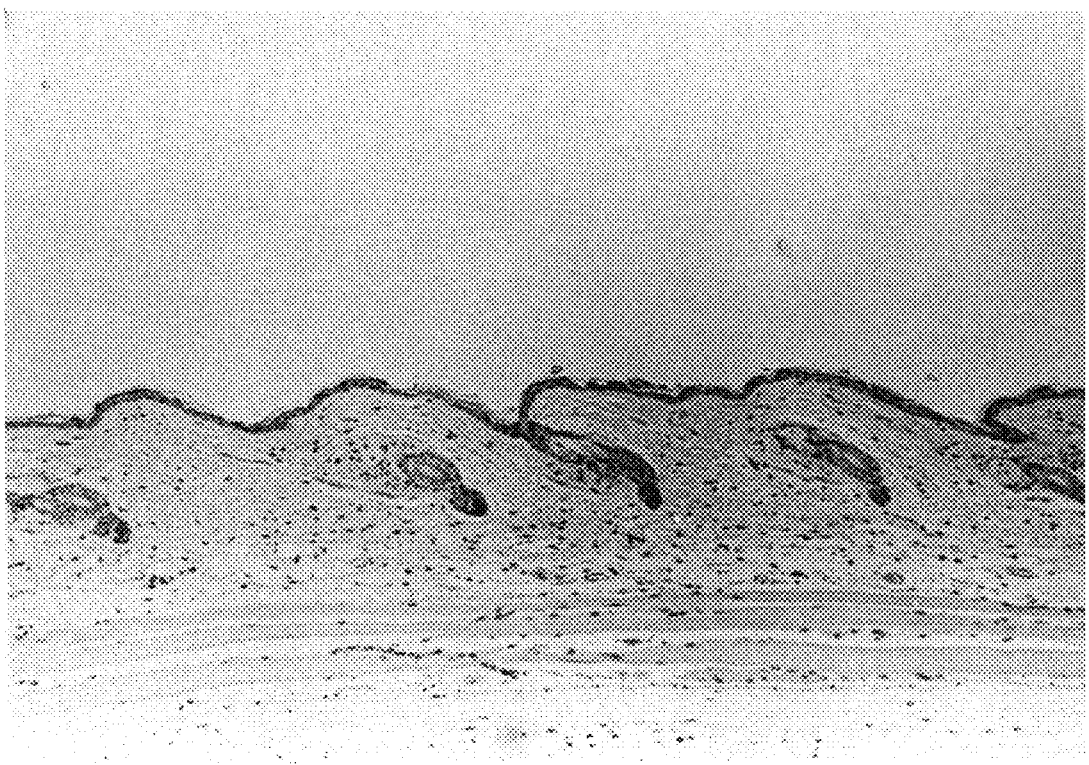
FIG. 6D is a photomicrograph of skin tissue from a mouse, where 10 nmol 17β-estradiol in 200 μL acetone was applied topically to shaved skin twice a week for five weeks. Tissue is stained with hematoxylin/eosin.
Figure 6E:
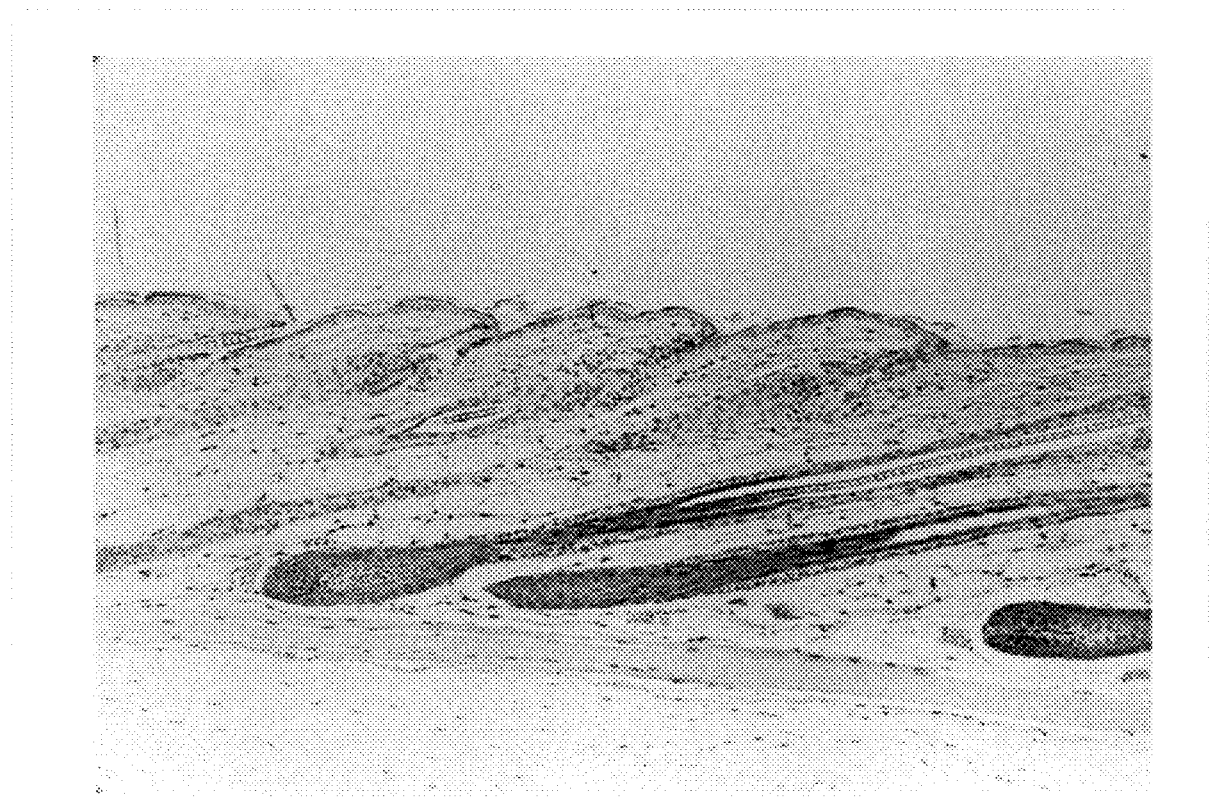
FIG. 6E is a photomicrograph of skin tissue from a mouse, where 200 μL of acetone was applied topically to shaved skin twice a week for seven weeks. Tissue is stained with hematoxylin/eosin
Figure 6F:
FIG. 6F is a photomicrograph of skin tissue from a mouse, where 10 nmol 17β-estradiol in 200 μL acetone was applied topically to shaved skin twice a week for seven weeks. Tissue is stained with hematoxylin/eosin.

In order to determine if 17-β-estradiol could influence hair growth, six week old CD-1 female mice were clipped on the dorsal surface with electric clippers and then treated twice weekly from the 6th week of age to the 16th week of age with topical applications of either (a) 10 nmol 17-β-estradiol or (b) acetone vehicle alone. Treatment with 17-β-estradiol had a potent inhibitory effect on dorsal hair regrowth. As shown in FIG. 5, 100% of the acetone-treated mice demonstrated full hair regrowth by 13 weeks of age. In contrast, mice treated with 17-β-estradiol did not demonstrate any full hair regrowth by 16 weeks of age. Some of the 17-β-estradiol-treated mice did demonstrate a partial patchy hair regrowth that involved less than 10% of the total clipped area. At 12 weeks of age, 20% of the 17-β-estradiol-treated mice demonstrated partial patchy hair regrowth and by 15 weeks 40% of the 17-β-estradiol-treated mice demonstrated such partial patchy hair regrowth (data not shown).

The above results demonstrate that 17-β-estradiol treatment just before and during the 2nd telogen phase potently blocked hair growth. In order to determine if 17-β-estradiol could block hair growth in pre-existing anagen follicles, 10 week old mice in the anagen phase of the hair cycle were treated twice weekly with 17-β-estradiol applied topically to clipped dorsal skin. Within two weeks it was apparent that the 17-β-estradiol-treated mice were no longer growing hair while all the acetone mice developed a full coat of hair (data not shown). Treatment with 17-β-estradiol was continued for 10 weeks and during this period no hair growth was apparent. The results of this experiment demonstrate that 17-β-estradiol can also block hair growth in mouse skin treated during the 3rd synchronous anagen phase.

EXAMPLE 6

Effect of 17-β-estradiol on the Hair Follicle Cycle

To determine the effect of 17-β-estradiol on the hair follicle cycle, mice were treated with 17-β-estradiol or acetone alone twice weekly from the 4th week of age to the 15th week of age. Every week, histological analysis of the skin from 3 mice from each group was conducted to determine the phase of the hair cycle. Representative skin histology sections from acetone- and 17-β-estradiol-treated mice at 7, 9, and 11 weeks of age are shown in FIGS. 6A–6F. As expected, at 7 weeks of age all follicles were in telogen in both the 17-β-estradiol and the acetone-treated mice. By 9 weeks of age, the hair follicles of the acetone control mice entered anagen while the hair follicles of the 17-β-estradiol mice remained in telogen. By 11 weeks of age, the hair follicles of the acetone treated mice were all in mid to late anagen while the hair follicles of the 17-β-estradiol-treated mice remained in telogen. At the termination of the experiment, when the mice were 15 weeks of age, the hair follicles of the 17-β-estradiol-treated mice were still arrested in telogen (data not shown). Collectively these data demonstrate that the topical application of 17-β-estradiol prevents hair re-growth by arresting the hair follicle in the telogen phase of the hair cycle.

The foregoing examples are illustrative of the present invention, and are not to be construed as limiting thereof. The invention is defined by the following claims, with equivalents of the claims to be included therein.

That which is claimed is:

1. A method of treating alopecia in a subject in need thereof comprising topically applying to the skin of said subject an estrogen receptor antagonist or a pharmaceutically acceptable salt thereof, wherein said estrogen receptor antagonist is a steroid, in an amount sufficient to treat alopecia.

2. A method according to claim 1, wherein said subject is a female subject.

3. A method according to claim 1, wherein said subject is a male subject.

4. A method according to claim 1, wherein said estrogen receptor antagonist is applied to the scalp of a subject.

5. A method according to claim 1, wherein said skin contains telogen-phase hair follicles.

6. A method according to claim 1, wherein said estrogen receptor antagonist is selected from the group consisting of 7α-[9-(4, 4, 5, 5, 5, -pentafluoropentylsulfinyl)nonyl]estra-1,3,5(10)-triene-3,17β-diol, N-n-butyl-N-methyl-11-(3,17β-dihydroxyestra-1,3,5(10)-triene-7α-yl)undecanamide, 11β-[4-[2-(dimethylaminoethoxy]phenyl]-estradiol, and N-methyl-N-isopropyl-(3,17β-dihydroxy-estra-1,2,5(10)-trien-11-β-yl)-undecamide.

7. A method of promoting hair growth in a subject in need thereof comprising topically applying to the skin of said subject a compound selected from the group consisting of an estrogen receptor antagonist or a pharmaceutically acceptable salt thereof, wherein said estrogen receptor antagonist is a steroid, in an amount sufficient to promote hair growth.

8. A method according to claim 7, wherein said subject is afflicted with hair loss, and said compound is administered in an amount effective to treat hair loss.

* * * * *

UNITED STATES PATENT AND TRADEMARK OFFICE
CERTIFICATE OF CORRECTION

PATENT NO. : 6,204,258 B1
DATED : March 20, 2001
INVENTOR(S) : Smart et al.

Page 1 of 1

It is certified that error appears in the above-identified patent and that said Letters Patent is hereby corrected as shown below:

Column 10,
Line 56, after "undecamide" insert -- , [6-hydroxy-2-(4-hydroxyphenyl)benzo[*b*]thien-3-yl] [4-[3-(1-pyrrolidinyl)ethoxy]phenyl]methanone, 3-[4(1,2-Diphenylbut-1-enyl) phenyl]acrylic acid, tamoxifen, clomiphene, and keoxifene. --.

Signed and Sealed this

Twenty-eighth Day of May, 2002

Attest:

*Attesting Officer*

JAMES E. ROGAN
*Director of the United States Patent and Trademark Office*